(12) United States Patent
Sasaki et al.

(10) Patent No.: US 12,175,561 B2
(45) Date of Patent: Dec. 24, 2024

(54) MEDICAL INFORMATION PROCESSING APPARATUS

(71) Applicant: CANON MEDICAL SYSTEMS CORPORATION, Otawara (JP)

(72) Inventors: Sho Sasaki, Utsunomiya (JP); Kazumasa Noro, Shioya-gun (JP); Yudai Yamazaki, Nasushiobara (JP); Kosuke Arita, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 425 days.

(21) Appl. No.: 17/571,771

(22) Filed: Jan. 10, 2022

(65) Prior Publication Data

US 2022/0230363 A1 Jul. 21, 2022

(30) Foreign Application Priority Data

Jan. 21, 2021 (JP) .................................. 2021-007941

(51) Int. Cl.

| G06T 11/00 | (2006.01) |
| G06T 7/00 | (2017.01) |
| G06V 10/764 | (2022.01) |
| G16H 30/40 | (2018.01) |
| A61B 6/50 | (2024.01) |
| A61B 90/00 | (2016.01) |

(52) U.S. Cl.
CPC ............ G06T 11/00 (2013.01); G06T 7/0014 (2013.01); G06V 10/764 (2022.01); G16H 30/40 (2018.01); *A61B 6/504* (2013.01); *A61B 90/39* (2016.02); *G06T 2207/30101* (2013.01); *G06V 2201/03* (2022.01)

(58) Field of Classification Search
CPC ............... G06T 7/0012; G06T 7/11; G06T 2207/10081; G06T 2207/30101; G06T 2207/20084; G06T 2207/10072; G06T 2207/20081; G06T 2207/10088; G06T 2207/30004; G06T 5/50; G06T 2207/10132
USPC ......................................... 382/128
See application file for complete search history.

(56) References Cited

U.S. PATENT DOCUMENTS

| 2010/0053342 A1* | 3/2010 | Hwang | .................. | H04N 23/58 |
| | | | | 348/207.99 |
| 2016/0125595 A1* | 5/2016 | Silbert | ...................... | G06T 7/11 |
| | | | | 382/131 |
| 2018/0092615 A1* | 4/2018 | Sakaguchi | ........... | A61B 6/5229 |
| 2018/0247408 A1* | 8/2018 | Wang | ........................ | G06T 7/35 |

FOREIGN PATENT DOCUMENTS

JP 2020-18705 A 2/2020

* cited by examiner

*Primary Examiner* — Ajibola A Akinyemi
(74) *Attorney, Agent, or Firm* — Oblon, McClelland, Maier & Neustadt, L.L.P.

(57) ABSTRACT

A medical information processing apparatus according to an embodiment includes a processing circuitry. The processing circuitry is configured to acquires one or more first images that are images of parts obtained by classifying a subject appearing in a medical image into each part, generates, from the acquired one or more first images, a second image that is an image of the subject spatially continuous according to an anatomical criterion, and synthesizes the generated second image with a background to generate a third image.

11 Claims, 5 Drawing Sheets

INPUT-SIDE
TRAINING DATA

NEURAL
NETWORK

OUTPUT-SIDE
TRAINING DATA

| CAPTURING DIRECTION | AHA NO. | BLOOD VESSEL IMAGE A | BLOOD VESSEL IMAGE B | ... |
|---|---|---|---|---|
| RAO View | 1 | PARTIAL IMAGE A1 | PARTIAL IMAGE B1 | ... |
| | 2 | PARTIAL IMAGE A2 | PARTIAL IMAGE B2 | ... |
| | ⋮ | ⋮ | ⋮ | ... |
| | 15 | PARTIAL IMAGE A15 | PARTIAL IMAGE B15 | ... |
| ⋮ | ⋮ | ⋮ | ⋮ | ⋮ |

MEDICAL INFORMATION PROCESSING APPARATUS

CROSS-REFERENCE TO RELATED APPLICATIONS

This application is based upon and claims the benefit of priority from Japanese Patent Application No. 2021-007941, filed on Jan. 21, 2021; the entire contents of which are incorporated herein by reference.

FIELD

Embodiments described herein relate generally to a medical information processing apparatus.

BACKGROUND

One of the issues to be solved by the embodiment disclosed in this specification and drawings is to support the generation of training data. However, the issue to be solved by the embodiment disclosed in this specification and drawings is not limited to the above-described issue. The issue corresponding to each advantageous effect of each configuration described in the embodiment below may be regarded as another issue.

DETAILED DESCRIPTION

A medical information processing apparatus according to the present embodiment will be described below with reference to the drawings. It is assumed that, in the embodiment below, the parts denoted by the same reference numeral perform the same operation and duplicate description will be omitted as appropriate.

First Embodiment

Figure 1:
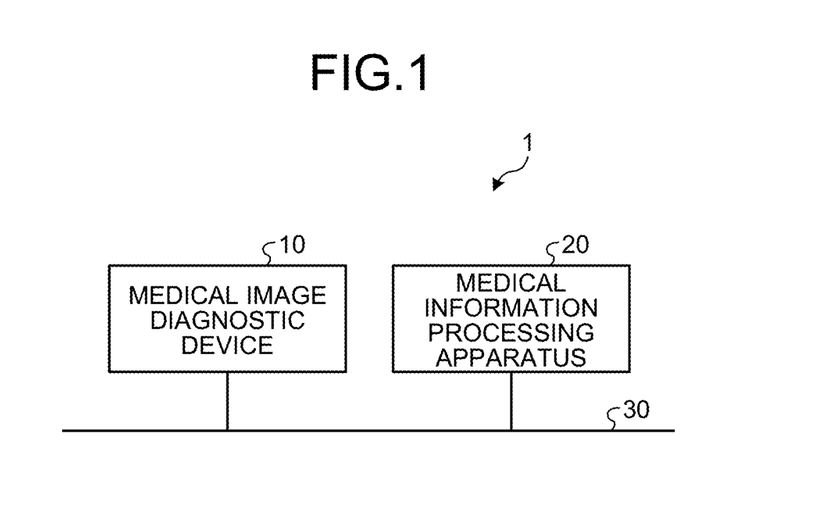
FIG. 1 is a block diagram illustrating an example of a configuration of a machine learning system according to a first embodiment.

FIG. 1 is a block diagram illustrating an example of a configuration of a machine learning system 1 according to a first embodiment. The machine learning system 1 includes a medical image diagnostic device 10 and a medical information processing apparatus 20. Each system and each device are communicatively connected to each other via a network 30. The configuration illustrated in FIG. 1 is an example, and the number of systems and devices may be optionally changed. A device not illustrated in FIG. 1 may be connected to the network 30.

The medical image diagnostic device 10 is a device that captures an image to examine a subject. For example, the medical image diagnostic device 10 is an X-ray diagnostic device (angiography) for a circulatory system. The medical image diagnostic device 10 is not limited to the X-ray diagnostic device (angiography) for a circulatory system but may also be an X-ray diagnostic device, an X-ray computed tomography (CT) device, a magnetic resonance imaging device, a nuclear medicine diagnostic device, an ultrasonic diagnostic device, etc.

The medical information processing apparatus 20 is implemented by a computer device such as a personal computer, a server, or a workstation. The medical information processing apparatus 20 generates training data for supervised learning in machine learning.

First, a trained model using the training data generated by the medical information processing apparatus 20 will be described. For example, a description will be given for a trained model with which, when the medical image data obtained by capturing a coronary artery by the medical image diagnostic device 10 is input, a blood vessel image indicating a blood vessel region of the medical image data is output.

Figure 2:
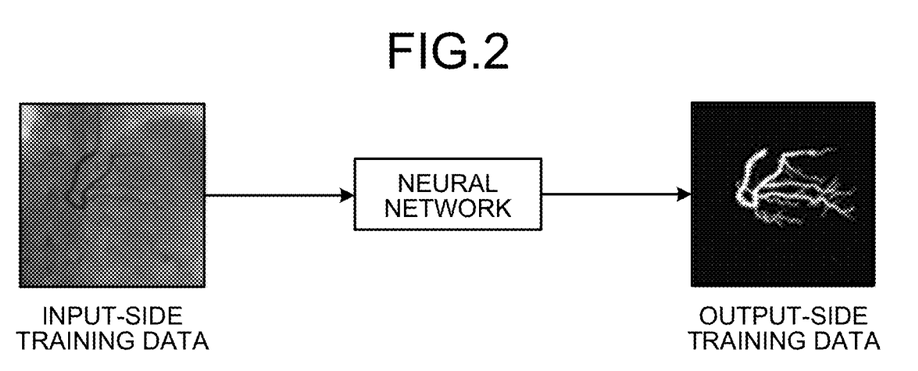
FIG. 2 is a diagram illustrating an example of supervised learning in machine learning.

FIG. 2 is a diagram illustrating an example of supervised learning in machine learning. In a neural network illustrated in FIG. 2, the medical image data obtained by capturing the coronary arteries by the medical image diagnostic device 10 is input as training data on the input side. In the neural network, the blood vessel image illustrating the blood vessel region of the medical image data is input as training data on the output side.

In this case, a technical person who creates the trained model needs to prepare the medical image data and the blood vessel image. However, as the blood vessel image is manually created by an expert, it takes a lot of time to create it. Furthermore, as an enormous amount of training data is needed to create the trained model, an enormous amount of time is needed. Thus, the medical information processing apparatus 20 generates the training data.

Next, the medical information processing apparatus 20 will be described.

Figure 3:
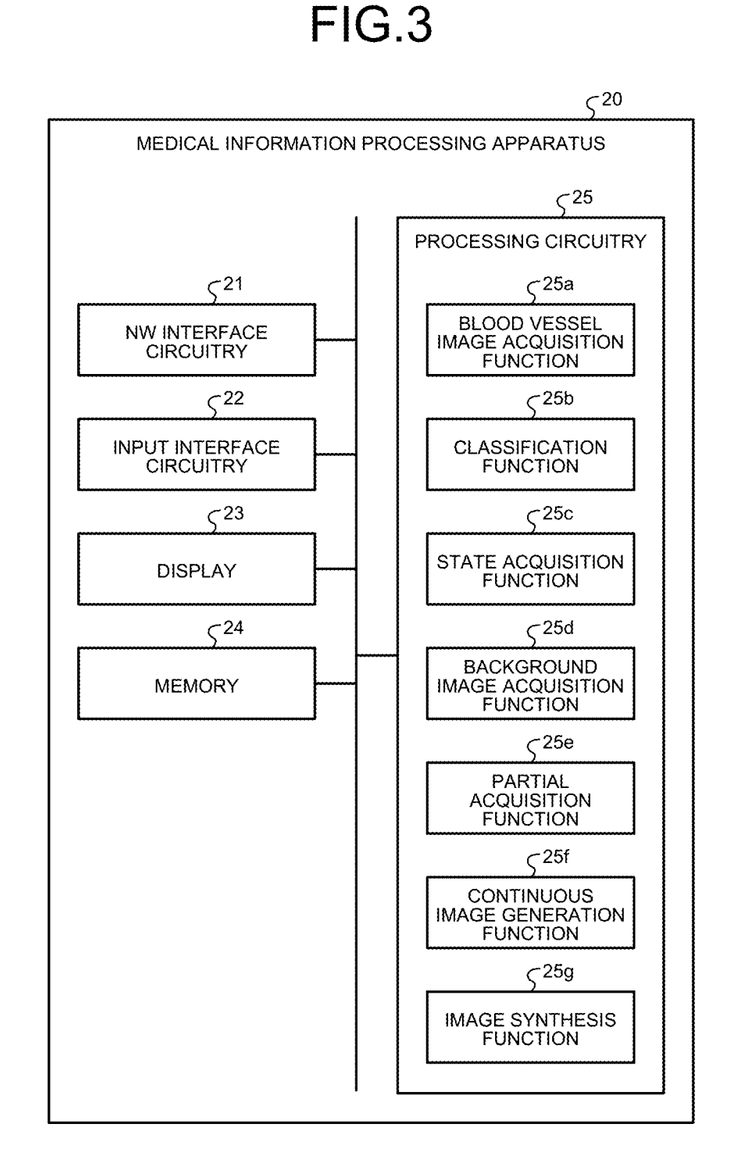
FIG. 3 is a block diagram illustrating an example of a configuration of a medical information processing apparatus according to the first embodiment.

FIG. 3 is a block diagram illustrating an example of a configuration of the medical information processing apparatus 20 according to the first embodiment. The medical information processing apparatus 20 includes a network (NW) interface circuitry 21, an input interface circuitry 22, a display 23, a memory 24, and a processing circuitry 25.

The NW interface circuitry 21 is connected to the processing circuitry 25 to control transmission and communication of various types of data performed with each device connected via the network 30. For example, the NW interface circuitry 21 is implemented by a network card, a network adapter, or a network interface controller (NIC).

The input interface circuitry 22 is connected to the processing circuitry 25 to convert an input operation received from an operator (medical practitioner) into an electric signal and outputs the electric signal to the processing circuitry 25. Specifically, the input interface circuitry 22 converts an input operation received from the operator into an electric signal and outputs the electric signal to the processing circuitry 25. For example, the input interface circuitry 22 is implemented by a trackball, a switch button, a mouse, a keyboard, a touch pad that performs an input operation by a touch on an operation surface, a touch screen having an integrated combination of a display screen and a touch pad, a non-contact input circuitry using an optical sensor, or a voice input circuitry. In this description, the input interface circuitry 22 is not limited to the one including a physical operating part such as a mouse and a keyboard. Examples of the input interface circuitry 22 include an electric signal processing circuitry that receives an electric signal corresponding to an input operation from an external input device provided separately from the apparatus and that outputs the electric signal to a control circuitry.

The display 23 is connected to the processing circuitry 25 to display various types of information and various types of image data output from the processing circuitry 25. For example, the display 23 is implemented by a liquid crystal display, a cathode ray tube (CRT) display, an organic EL display, a plasma display, or a touch panel.

The memory 24 is connected to the processing circuitry 25 to store various types of data. The memory 24 stores various programs that are read out and executed by the processing circuitry 25 to perform various functions. For example, the memory 24 is implemented by a semiconductor memory device such as a random access memory (RAM) or a flash memory, a hard disk, or an optical disk.

The processing circuitry 25 controls the overall operation of the medical information processing apparatus 20. The processing circuitry 25 has, for example, a blood vessel image acquisition function 25a, a classification function 25b, a state acquisition function 25c, a background image acquisition function 25d, a partial acquisition function 25e, a continuous image generation function 25f, and an image synthesis function 25g. According to the embodiment, the memory 24 stores, in the form of program executable by a computer, each of the processing functions performed by the blood vessel image acquisition function 25a, the classification function 25b, the state acquisition function 25c, the background image acquisition function 25d, the partial acquisition function 25e, the continuous image generation function 25f, and the image synthesis function 25g, which are components. The processing circuitry 25 is a processor that reads out a program from the memory 24 and executes the program to perform the function corresponding to each program. In other words, the processing circuitry 25 having read out each program has each function illustrated in the processing circuitry 25 of FIG. 3.

In the description of FIG. 3, the single processor performs the blood vessel image acquisition function 25a, the classification function 25b, the state acquisition function 25c, the background image acquisition function 25d, the partial acquisition function 25e, the continuous image generation function 25f, and the image synthesis function 25g, but a plurality of independent processors may be combined to form the processing circuitry 25, and each processor may execute a program to perform the function. In the description of FIG. 3, the single memory such as the memory 24 stores the program corresponding to each processing function, but a configuration may be such that a plurality of storage circuitries is distributed and arranged and the processing circuitry 25 reads out the corresponding program from the individual storage circuitries.

The term "processor" used in the above description refers to, for example, a central processing unit (CPU), a graphical processing unit (GPU), or a circuit such as an application specific integrated circuit (ASIC) or a programmable logic device (e.g., a simple programmable logic device (SPLD), a complex programmable logic device (CPLD), or a field programmable gate array (FPGA)). The processor reads out and executes the program stored in the memory 24 to perform the function. A configuration may be such that, instead of storing the program in the memory 24, the program is directly installed in a circuitry of the processor. In this case, the processor reads out and executes the program installed in the circuitry to perform the function.

The blood vessel image acquisition function 25a acquires a blood vessel image that is an image of a blood vessel. The blood vessel image acquisition function 25a may acquire the blood vessel image via the network 30, may acquire the blood vessel image from a connected storage medium, or may acquire the blood vessel image by other methods.

The classification function 25b classifies each part of the subject appearing in the medical image. For example, the classification function 25b classifies each part of a blood vessel included in the blood vessel image. The classification function 25b is an example of a classification unit. Here, the blood vessels included in the blood vessel image have different shapes in each capturing direction of the blood vessel image. Therefore, the classification function 25b classifies each part of the blood vessel in each capturing direction of the blood vessel image.

More specifically, the classification function 25b classifies each part of the blood vessel in the blood vessel image based on, for example, an operation received by the input interface circuitry 22. The classification function 25b may execute classification by other methods as well as the operation. For example, the classification function 25b may execute classification by using a trained model that classifies each part of the blood vessel in the blood vessel image.

Figure 4:
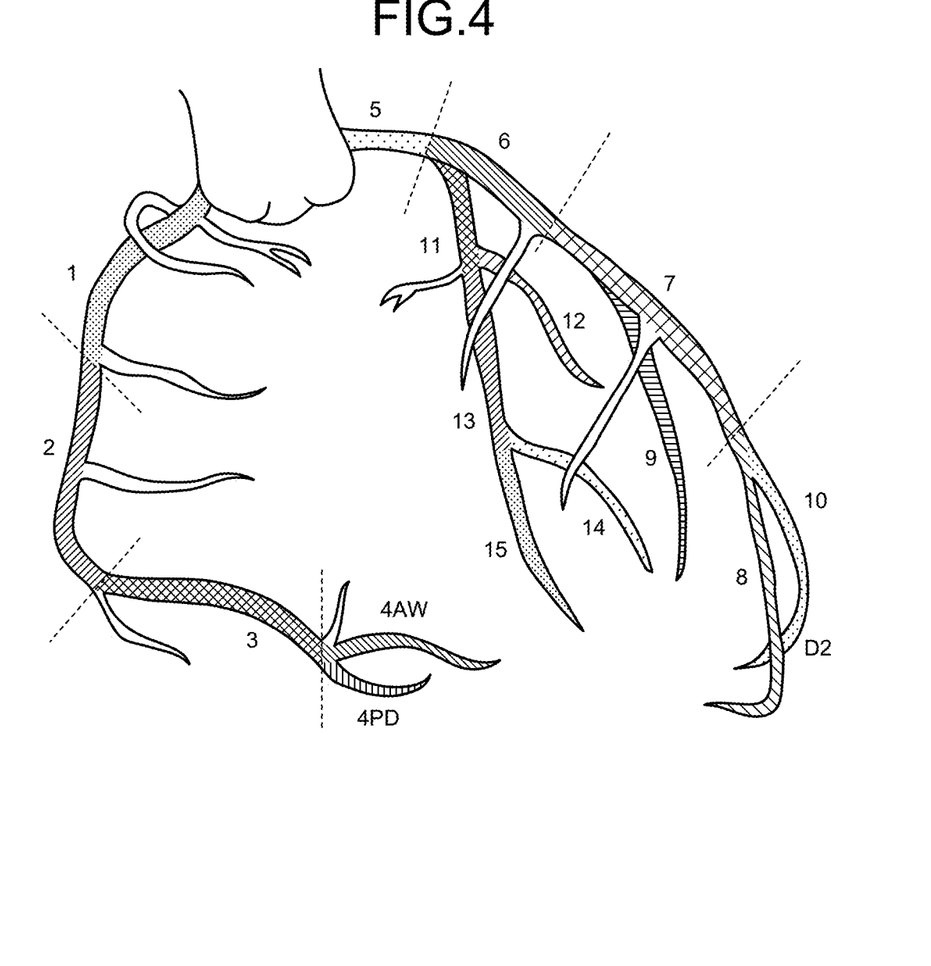
FIG. 4 is a diagram illustrating AHA classification in coronary arteries.

For example, the classification function 25b classifies each part of the subject in the medical image based on anatomical classification. Here, the classification function 25b classifies a blood vessel. Specifically, the classification function 25b classifies each part of the blood vessel in the blood vessel image based on the anatomical classification. For example, the classification function 25b classifies each part of the blood vessel in the blood vessel image based on the American Heart Association (AHA) classification in each capturing direction. Here, FIG. 4 is a diagram illustrating the AHA classification of the coronary arteries. As illustrated in FIG. 4, numbers 1 to 15 are assigned to the respective parts of the blood vessels in the coronary arteries. That is, each part of the blood vessels is classified.

Figure 5:
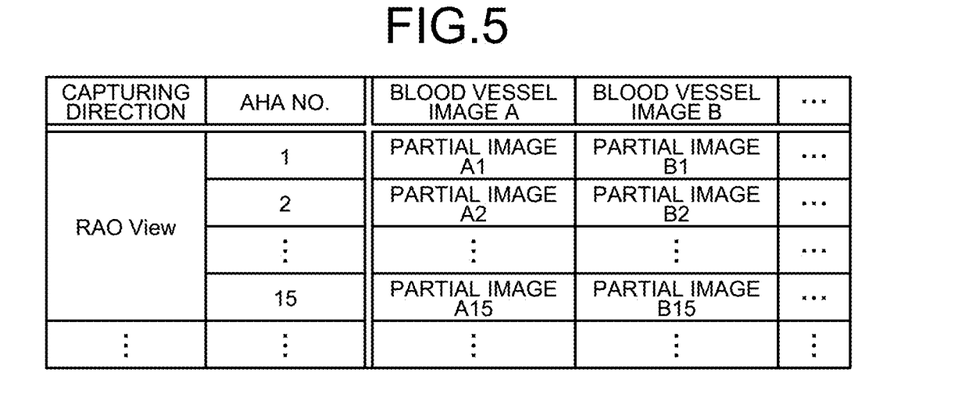
FIG. 5 is a table illustrating an example of a data structure of blood vessel partial information according to the first embodiment.

When the classification is executed, the classification function 25b registers each part of the blood vessel in the blood vessel image in blood vessel partial information. Here, FIG. 5 is a table illustrating an example of a data structure of the blood vessel partial information according to the first embodiment. The blood vessel partial information registers the partial image of a part of the blood vessel in each blood vessel image for each capturing direction of the blood vessel image and for each AHA number indicating each part of the blood vessel. Accordingly, the partial acquisition function 25e, which is described below, may acquire the image of a blood vessel of each part.

The state acquisition function 25c acquires blood vessel state information indicating the state of a blood vessel. The state acquisition function 25c is an example of a second acquisition unit. The blood vessel state information is information indicating the state of a blood vessel in the training data to be generated. For example, the blood vessel state information is information in which the degree of stenosis is set for each part of the blood vessel. That is, the state acquisition function 25c acquires the blood vessel state information indicating the degree of stenosis of the blood vessel. The state acquisition function 25c may acquire the blood vessel state information via the network 30, may acquire the blood vessel state information from a connected storage medium, or may acquire the blood vessel state information by other methods.

The background image acquisition function 25d acquires a background image serving as the background of the image of one or more parts of the blood vessel. The training data on the output side illustrated in FIG. 2 is obtained by extracting the image of the blood vessels from the training data on the input side. That is, the training data on the output side is the image of the blood vessels. Meanwhile, the training data on the input side includes not only the blood vessels but also various things such as organ. The background image is an image serving as the training data on the input side due to the synthesis with the image of the blood vessel. For example, the background image is a non-contrast image. The background image acquisition function 25d may acquire the background image via the network 30, may acquire the background image from a connected storage medium, or may acquire the background image by other methods.

The partial acquisition function 25e acquires one or more partial images that are images of parts obtained by classifying the subject appearing in the medical image into each part. For example, the partial acquisition function 25e acquires a partial image from the blood vessel image. Specifically, the partial acquisition function 25e acquires one or more partial images, which are images of parts of the blood vessel, from the blood vessel image that is the image of the blood vessel classified into each part. The partial acquisition function 25e is an example of a first acquisition unit. The partial image is an example of a first image. That is, the partial acquisition function 25e acquires a partial image from the blood vessel partial information.

Here, the blood vessel image has a different shape in each capturing direction in which the blood vessel is captured. For this reason, it is difficult to connect partial images in the blood vessel images having different capturing directions. Therefore, the partial acquisition function 25e acquires the partial image in each capturing direction in which the subject is captured. For example, the partial acquisition function 25e acquires the partial image in each capturing direction in which the blood vessel is captured. That is, the partial acquisition function 25e acquires the partial image from the blood vessel image having the identical capturing direction.

More specifically, the partial acquisition function 25e acquires the partial images of the respective blood vessel parts having the AHA numbers 1 to 15 from the blood vessel partial information. When the partial image is acquired from the blood vessel partial information, the partial acquisition function 25e may acquire the partial image from the identical blood vessel image, may acquire the partial image from the randomly selected blood vessel images, or may acquire the partial image from the blood vessel images selected according to a specific rule. Alternatively, the partial acquisition function 25e may acquire the partial image from the blood vessel image whose capturing condition such as a luminance value or an X-ray condition is close to the capturing condition for the training data to be generated.

Alternatively, the partial acquisition function 25e may acquire one or more partial images that match the condition specified by the blood vessel state information. Here, the state of the blood vessel in the training data to be generated is set in the blood vessel state information. That is, the condition for specifying the partial image to be acquired is set in the blood vessel state information. Therefore, the partial acquisition function 25e acquires one or more partial images from the blood vessel partial information based on the blood vessel state information.

For example, it is assumed that the blood vessel state information includes the settings that the contrast agent is injected from the blood vessel with AHA No. 1 and the degree of stenosis of the blood vessel with AHA No. 3 is 100°. When the contrast agent is injected from the blood vessel with AHA No. 1, the blood vessels Nos. 5 to 15 are not enhanced as the contrast agent does not enter. Furthermore, as the blood vessel with AHA No. 3 is clogged, the blood vessel with No. 3 and the subsequent vessels are not enhanced as the contrast agent does not enter. Therefore, the partial acquisition function 25e acquires the partial images of the blood vessels with AHA Nos. 1 and 2 specified by the blood vessel state information.

The partial acquisition function 25e generates a continuous image, which is an image of the subject spatially continuous according to an anatomical criterion, from one or more partial images acquired by the partial acquisition function 25e. For example, the partial acquisition function 25e acquires a partial image from the blood vessel image. Specifically, the continuous image generation function 25f generates a continuous image, which is an image of the blood vessel spatially continuous according to the anatomical criterion, from one or more partial images acquired by the partial acquisition function 25e. The continuous image generation function 25f is an example of a generation unit. The continuous image is an example of a second image. That is, the continuous image generation function 25f generates a continuous image that is spatially continuous. In other words, the continuous image generation function 25f does not connect blood vessels that would not normally be connected according to the anatomical criterion. When the partial acquisition function 25e acquires one partial image, the continuous image generation function 25f generates a continuous image that is a continuous blood vessel image formed by the one partial image. When the partial acquisition function 25e acquires a plurality of partial images, the continuous image generation function 25f generates a continuous image that is a continuous blood vessel image formed by the plurality of partial images.

For the connection portion of the blood vessel between the partial images, the continuous image generation function 25f adjusts the luminance value by weighted average, or the like, or executes non-rigid alignment so as to match the blood vessel diameters. Accordingly, the continuous image generation function 25f makes the smooth image of the connection portion of the blood vessel between the partial images.

The continuous image generation function 25f generates the continuous image having the state indicated by the blood vessel state information. For example, when the degree of stenosis of the blood vessel is set in the blood vessel state information, the continuous image generation function 25f generates the continuous image of the blood vessel having the degree of stenosis indicated by the blood vessel state information. For example, when the blood vessel state information has the settings of 90% as the degree of stenosis with AHA No. 2, the continuous image generation function 25f generates the continuous image in which the blood vessel diameter of the blood vessel in the partial image with AHA No. 2 is changed from 10% to 15%.

The image synthesis function 25g synthesizes the continuous image generated by the continuous image generation function 25f with the background to generate the synthesis image. The image synthesis function 25g is an example of an image synthesis unit. Specifically, the image synthesis function 25g synthesizes the continuous image generated by the continuous image generation function 25f with the background image serving as the background to generate the synthesis image. The background image is an example of a fourth image. The synthesis image is an example of a third image. For example, the synthesis image is used as the training data on the input side illustrated in FIG. 2.

Next, the processing flow for generating the training data by the medical information processing apparatus 20 will be described.

Figure 6:
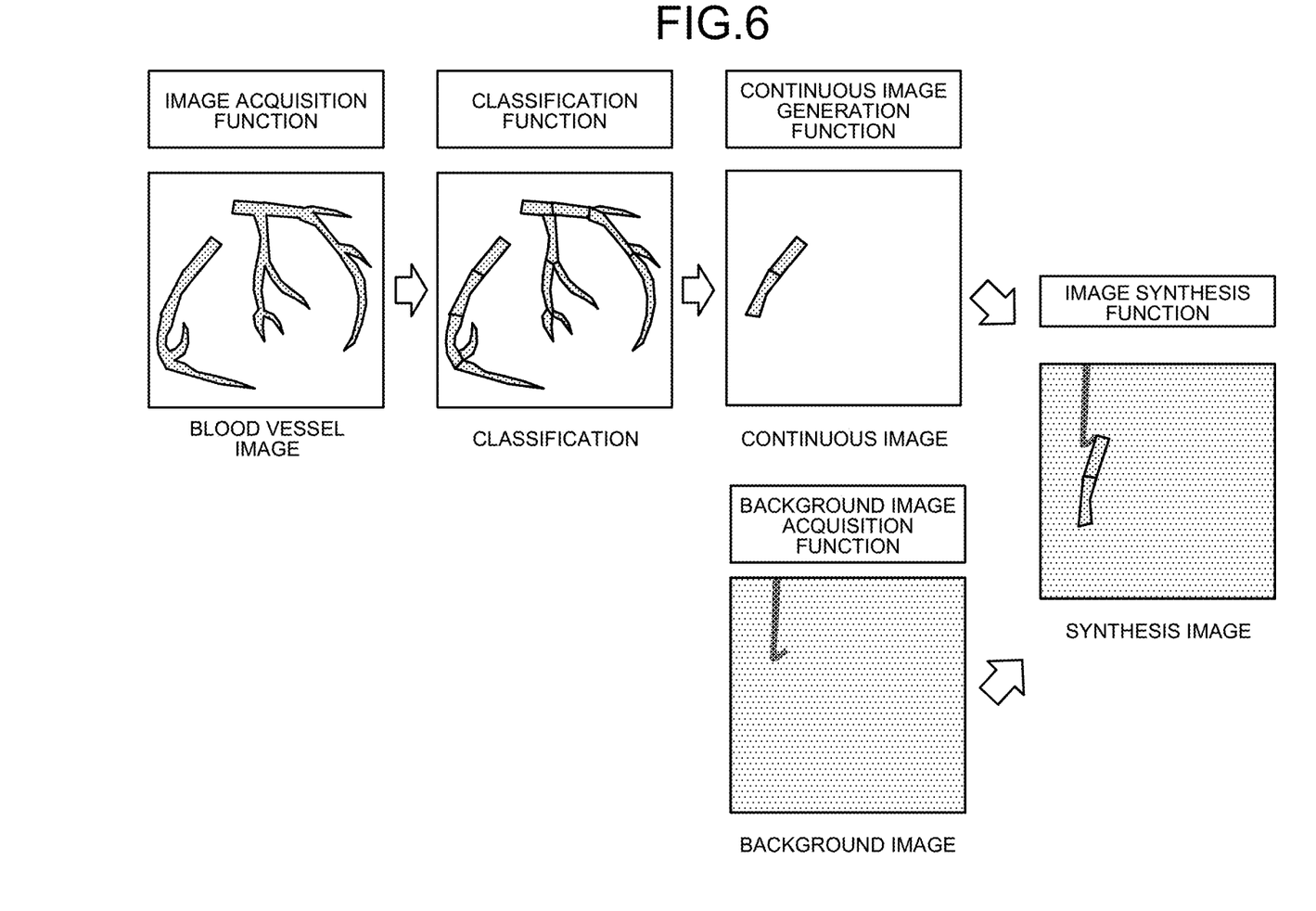
FIG. 6 is a diagram illustrating a processing flow for generating training data executed by the medical information processing apparatus according to the first embodiment.

FIG. 6 is a diagram illustrating the processing flow for generating the training data executed by the medical information processing apparatus 20 according to the first embodiment.

The blood vessel image acquisition function 25a acquires the blood vessel image.

The classification function 25b classifies each part of the blood vessel in the blood vessel image. The classification function 25b registers, in the blood vessel partial information, each part of the blood vessel in the blood vessel image.

The continuous image generation function 25f connects the blood vessels of the partial images acquired by the partial acquisition function 25e to generate the continuous image.

The background image acquisition function 25d acquires the background image.

The image synthesis function 25g synthesizes the continuous image with the background image to generate the synthesis image.

The synthesis image is used for, for example, the training data on the input side illustrated in FIG. 2. The continuous image is used for, for example, the training data on the output side illustrated in FIG. 2.

Next, the generation process executed by the medical information processing apparatus 20 will be described.

Figure 7:
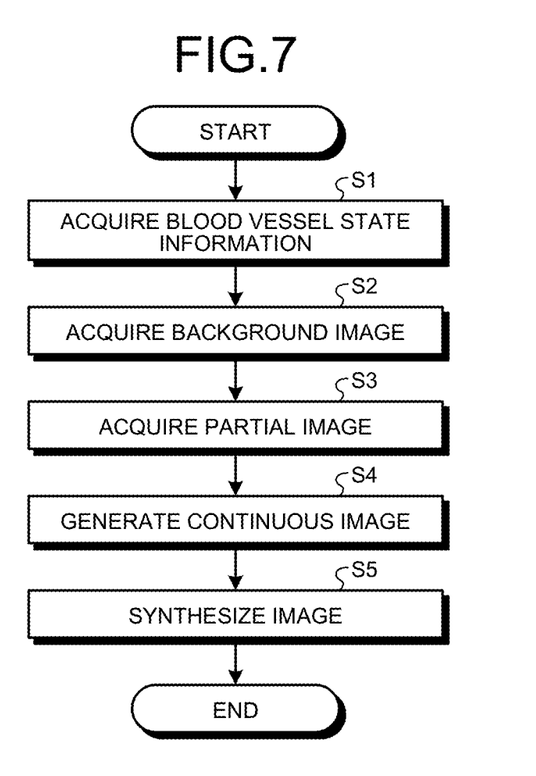
FIG. 7 is a flowchart illustrating an example of a generation process executed by the medical information processing apparatus according to the first embodiment.

FIG. 7 is a flowchart illustrating an example of the generation process executed by the medical information processing apparatus 20 according to the first embodiment. The generation process is a process to generate the synthesis image. It is assumed that each part of the blood vessel in the blood vessel image is classified in the blood vessel partial information.

The state acquisition function 25c acquires the blood vessel state information indicating the state of the blood vessel in the generated training data (Step S1).

The background image acquisition function 25d acquires the background image (Step S2).

The partial acquisition function 25e acquires one or more partial images based on the blood vessel state information (Step S3).

The continuous image generation function 25f connects the blood vessels of the acquired one or more partial images to generate the continuous image (Step S4).

The image synthesis function 25g synthesizes the background image with the continuous image to generate the synthesis image (Step S5).

Thus, the medical information processing apparatus 20 ends the generation process.

As described above, the medical information processing apparatus 20 according to the first embodiment acquires the partial image, which is the image of a part of the blood vessel, from the blood vessel image that is the image of the blood vessel classified into each part. The medical information processing apparatus 20 connects the acquired partial images to generate the continuous image that is the image of the blood vessels spatially continuous according to the anatomical criterion. Then, the medical information processing apparatus 20 synthesizes the continuous image with the background image to generate the synthesis image. Accordingly, the medical information processing apparatus 20 generates the synthesis image serving as the input-side training data and the continuous image serving as the output-side training data. Thus, the medical information processing apparatus 20 may support the generation of the training data.

Modification 1

In the description according to the first embodiment, the classification function 25b of the medical information processing apparatus 20 classifies a blood vessel according to the AHA classification. However, the classification function 25b may execute classification by other methods as well as the AHA classification. For example, the classification function 25b may classify each part of the blood vessel in the blood vessel image based on the shape of the blood vessel. Specifically, the classification function 25b may execute classification by performing pattern matching, or the like, to compare the shapes of blood vessels in each capturing direction.

More specifically, the classification function 25b of the medical information processing apparatus 20 acquires a two-dimensional blood vessel model indicating the shape of the blood vessel in each part by the AHA classification. The two-dimensional blood vessel model is generated by projecting a three-dimensional blood vessel model indicating the AHA classification onto a two-dimensional plane in each capturing direction. Then, the classification function 25b aligns the blood vessel image with the two-dimensional blood vessel model and considers the distance between the blood vessel image and the two-dimensional blood vessel model to classify each part of the blood vessel included in the blood vessel image.

Modification 2

According to the first embodiment, the continuous image generation function 25f of the medical information processing apparatus 20 generates the continuous image that is the image of blood vessels spatially continuous according to the anatomical criterion. Furthermore, the continuous image generation function 25f may specify the range for generating the image of the blood vessel based on the position information indicating the position of an insert that is inserted into the blood vessel. Then, the continuous image generation function 25f generates the continuous image, which is the image of the continuous blood vessels, in the specified range.

Here, an angiographic examination is performed in which a catheter is inserted to the destination of the blood vessel of the heart and a contrast agent is injected into the blood vessel through the catheter at the destination to examine the state of the blood vessel and blood flow. In such an angiographic examination, or the like, the contrast agent is sometimes not injected into the blood vessel until the catheter reaches the destination. In this case, a medical practitioner such as a doctor inserts the catheter to the destination while looking at the non-contrast image. That is, the medical practitioner inserts the catheter to the destination with the image in which the blood vessel is not clear.

Therefore, the medical information processing apparatus 20 uses the continuous image and the synthesis image to generate the trained model for generating the image indicating the shape of the blood vessel. Specifically, when the non-contrast image is input, the medical information processing apparatus 20 generates the trained model for outputting the image indicating the shape of the blood vessel included in the non-contrast image. Then, the medical information processing apparatus 20 superimposes the image indicating the shape of the blood vessel on the non-contrast image.

However, displaying all the blood vessels in the input non-contrast image may be complicated. That is, visibility may be improved by hiding unnecessary blood vessels. For example, it is not necessary to display a blood vessel to which an insert such as a catheter has been delivered or a blood vessel in a direction in which an insert such as a catheter is not expected to proceed. Therefore, the medical information processing apparatus 20 displays a blood vessel within a range of set distance with respect to the traveling direction of the insert from the blood vessel into which the insert such as a catheter has been inserted.

Therefore, the partial acquisition function 25e acquires one or more partial images specified by the insert inserted into the blood vessel. Then, the continuous image generation function 25f specifies the range for generating the continuous image based on the position information indicating the position of the insert inserted into the blood vessel. Specifically, the continuous image generation function 25f generates the continuous image of the blood vessel within the range of set distance with respect to the traveling direction of the insert from the position information indicating the position of the insert inserted into the blood vessel. By using the thus generated continuous image and the synthesis image, the medical information processing apparatus 20 generates the trained model for generating the image illustrating the shape of the blood vessel. Accordingly, when the non-contrast image in which the insert such as a catheter is inserted is input, the trained model outputs the image illustrating the shape of the blood vessel within the range of set distance with respect to the traveling direction of the insert.

Modification 3

The continuous image generation function 25f may generate a medical image in which a plurality of devices is placed in blood vessels. For example, a stent placed in a blood vessel has one or more pairs of markers attached thereto. The stent marker is detected from the medical image so that the medical image is used for various types of processing. Thus, there is a need for a trained model capable of detecting a stent marker.

Here, the medical image may include one or more sets of stent markers. Therefore, the trained model for detecting stent markers is preferably trained with a medical image including a plurality of stent markers. Unfortunately, there are relatively few medical images including a plurality of stent markers.

Therefore, the partial acquisition function 25e acquires a partial image of the blood vessel in which a device such as a stent is placed. Specifically, the partial acquisition function 25e acquires one or more partial images including device markers of the device placed in the blood vessel. Then, the continuous image generation function 25f connects the partial images of the blood vessels, in which the devices are placed, to generate the continuous image. That is, the continuous image generation function 25f generates the continuous image from the partial images including the device markers. Therefore, the medical information processing apparatus 20 may generate the medical image in which the plurality of devices is placed in the blood vessels.

Modification 4

In the example described according to the first embodiment, the modification 1, the modification 2, and the modification 3, the part of the subject is a blood vessel. However, the part of the subject is not limited to the blood vessel and may be another part. For example, the part of the subject may be a gastrointestinal tract, an organ, a bone, or a muscle.

Modification 5

In the description according to the first embodiment, the modification 1, the modification 2, and the modification 3, the medical information processing apparatus 20 includes the blood vessel image acquisition function 25a, the classification function 25b, the state acquisition function 25c, the background image acquisition function 25d, the partial acquisition function 25e, the continuous image generation function 25f, and the image synthesis function 25g. However, all or some of these functions may be included in another apparatus as well as the medical information processing apparatus 20. For example, these functions may be included in a computer device such as a personal computer, a server, or a workstation. These functions may be distributed to different apparatuses or systems.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing apparatus comprising processing circuitry configured to:
   acquire a plurality of first images and a plurality of labels in an associated manner, each of the first images being an image of a part obtained by classifying a subject appearing in a medical image into each part, and each of the labels indicating a classification of the first image;
   receive selections of a plurality of labels;
   generate a second image, the second image being an image obtained by connecting together respective parts of some of the plurality of first images acquired that are associated with the plurality of labels selected; and
   synthesize the generated second image with a background to generate a third image.

2. The medical information processing apparatus according to claim 1, wherein the processing circuitry is further configured to acquire the plurality of first images in each capturing direction in which the subject is captured.

3. The medical information processing apparatus according to claim 1, wherein the processing circuitry is further configured to classify each part of the subject appearing in the medical image.

4. The medical information processing apparatus according to claim 3, wherein the processing circuitry is further configured to classify each part of the subject in the medical image based on anatomical classification.

5. The medical information processing apparatus according to claim 3, wherein the processing circuitry is further configured to classify each part of the subject in the medical image based on a shape of each part of the subject.

6. The medical information processing apparatus according to claim 1, wherein the processing circuitry is further configured to;
   acquire the plurality of first images, which are images of parts of a blood vessel of the subject, from a blood vessel image obtained by classifying the blood vessel into each part; and generate the second image that is an image of a blood vessel spatially continuous according to an anatomical criterion.

7. The medical information processing apparatus according to claim 6, wherein the processing circuitry is further configured to:
    acquire blood vessel state information indicating a state of a blood vessel; and
    acquire the plurality of first images that match a condition specified by the blood vessel state information.

8. The medical information processing apparatus according to claim 7, wherein the processing circuitry is further configured to;
    acquire the blood vessel state information indicating a degree of stenosis of a blood vessel; and
    generate the second image of the blood vessel having the degree of stenosis indicated by the blood vessel state information.

9. The medical information processing apparatus according to claim 6, wherein the processing circuitry is further configured to:
    acquire the plurality of first images specified by an insert inserted into a blood vessel; and
    specify a range for generating the second image from the first image based on position information indicating a position of an insert inserted into the blood vessel.

10. The medical information processing apparatus according to claim 6, wherein the processing circuitry is further configured to:
    acquire the plurality of first images including a device marker of a device placed in a blood vessel; and
    generate the second image from the first images including the device marker.

11. The medical information processing apparatus according to claim 1, wherein the processing circuitry is further configured to synthesize the second image with a non-contrast image serving as a background to generate the third image.

\* \* \* \* \*